(12) United States Patent
Bolton et al.

(10) Patent No.: US 8,283,387 B2
(45) Date of Patent: Oct. 9, 2012

(54) PROCESS FOR THE CONVERSION OF SYNTHESIS GAS TO OXYGENATES

(75) Inventors: Leslie W. Bolton, Fleet (GB); Benjamin P. Gracey, Hull (GB)

(73) Assignee: BP Chemicals Limited, Middlesex (GB)

( * ) Notice: Subject to any disclaimer, the term of this patent is extended or adjusted under 35 U.S.C. 154(b) by 729 days.

(21) Appl. No.: 12/227,646

(22) PCT Filed: May 25, 2007

(86) PCT No.: PCT/GB2007/001980
§ 371 (c)(1),
(2), (4) Date: Jun. 11, 2009

(87) PCT Pub. No.: WO2007/138303
PCT Pub. Date: Dec. 6, 2007

(65) Prior Publication Data
US 2010/0016453 A1    Jan. 21, 2010

(30) Foreign Application Priority Data
Jun. 1, 2006    (EP) .................................... 06252833

(51) Int. Cl.
*C07C 27/00*    (2006.01)
(52) U.S. Cl. .......................... 518/705; 518/714; 518/715

(58) Field of Classification Search ................ 518/705, 518/714, 715
See application file for complete search history.

(56) References Cited

U.S. PATENT DOCUMENTS

| | | | |
|---|---|---|---|
| 4,011,275 A | 3/1977 | Zahner | |
| 4,831,060 A | 5/1989 | Stevens et al. | |
| 2007/0155999 A1* | 7/2007 | Pujado et al. | 585/327 |
| 2010/0069515 A1* | 3/2010 | Tirtowidjojo et al. | 518/705 |

OTHER PUBLICATIONS

International Search Report for PCT/GB2007/001980, mailed Oct. 2, 2007.
Written Opinion of the International Searching Authority for PCT/GB2007/001980, mailed Oct. 2, 2007.

* cited by examiner

*Primary Examiner* — Jafar Parsa
(74) *Attorney, Agent, or Firm* — Nixon & Vanderhye

(57) ABSTRACT

Process for converting carbon oxide(s) and hydrogen containing feedstocks to oxygen containing hydrocarbon compounds, in the presence of a particulate catalyst, by reacting carbon oxide(s) and hydrogen in the presence of a particulate catalyst in a conversion reactor to form products containing oxygen containing hydrocarbon compounds. Ether(s) selected from ethyl, propyl and butyl ether are added and reacted inside the conversion reactor.

15 Claims, No Drawings

PROCESS FOR THE CONVERSION OF SYNTHESIS GAS TO OXYGENATES

This application is the U.S. national phase of International Application No. PCT/GB2007/001980, filed 25 May 2007, which designated the U.S. and claims priority to European Application No. 06252833.6, filed 1 Jun. 2006, the entire contents of each of which are hereby incorporated by reference.

The present invention relates to an improved process for the conversion of carbon oxide(s) and hydrogen containing feedstocks to oxygen containing hydrocarbon compounds in the presence of a particulate catalyst.

In particular, the present invention relates to an improved process for the conversion of carbon oxide(s) (CO and CO2) and hydrogen containing feedstocks, e.g. synthesis gas or syngas, to alcohols in the presence of a particulate modified molybdenum sulphide based catalyst, and/or a modified methanol based catalyst and/or a modified Fischer-Tropsch catalyst and/or a precious metal based catalyst, such as rhodium.

U.S. Pat. No. 4,122,110 relates to a process for manufacturing alcohols, particularly linear saturated primary alcohols, by reacting carbon monoxide with hydrogen at a pressure between 20 and 250 bars and a temperature between 150° C. and 400° C., in the presence of a catalyst, characterized in that the catalyst contains at least 4 essential components: (a) copper (b) cobalt (c) at least one element M selected from chromium, iron, vanadium and manganese, and (d) at least one alkali metal.

U.S. Pat. No. 4,831,060 relates to the production of mixed alcohols from carbon monoxide and hydrogen gases using a catalyst, with optionally a co-catalyst, wherein the catalyst metals are molybdenum, tungsten or rhenium, and the co-catalyst metals are cobalt, nickel or iron.

The catalyst is promoted with a Fischer-Tropsch promoter like an alkali or alkaline earth series metal or a smaller amount of thorium and is further treated by sulfiding. The composition of the mixed alcohols fraction can be selected by selecting the extent of intimate contact among the catalytic components.

Journal of Catalysis 114, 90-99 (1988) discloses a mechanism of ethanol formation from synthesis gas over CuO/ZnO/Al2O3. The formation of ethanol from CO and H2 over a CuO/ZnO methanol catalyst is studied in a fixed-bed microreactor by measuring the isotopic distribution of the carbon in the product ethanol when C(13) methanol was added to the feed.

It is an object of the present invention to provide an improved process in terms of selectivity and catalyst activity and operating life for the conversion of carbon oxide(s) and hydrogen containing feedstocks to oxygen containing hydrocarbon compounds in the presence of a particulate catalyst. Where, a particulate catalyst is defined as being either a supported or unsupported heterogeneous catalyst.

In particular, the present invention relates to an improved process in terms of selectivity and catalyst activity and operating life, for the conversion of carbon oxide(s) and hydrogen containing feedstocks, e.g. synthesis gas or syngas, to alcohols in the presence of a particulate catalyst; whereby the said particulate catalyst may comprise any one or more of the following: a modified molybdenum sulphide based catalyst; and/or a modified methanol based catalyst; and/or a modified Fischer-Tropsch catalyst; and/or a precious metal based catalyst, such as rhodium.

The present invention thus provides a process for the conversion of carbon oxide(s) and hydrogen containing feedstocks to oxygen containing hydrocarbon compounds in the presence of a particulate catalyst, comprising the step of reacting carbon oxide(s) and hydrogen in the presence of a particulate catalyst in a conversion reactor to form products comprising oxygen containing hydrocarbon compounds; characterised in that ether(s) are added and reacted inside the conversion reactor.

In particular, the present invention provides a process for the conversion of carbon oxide(s) and hydrogen containing feedstocks, e.g. synthesis gas or syngas, to alcohols in the presence of a particulate modified molybdenum sulphide based catalyst and/or a modified methanol based catalyst and/or a modified Fischer-Tropsch catalyst and/or a precious metal based catalyst (e.g. rhodium), comprising the step of reacting carbon monoxide and hydrogen in the presence of said catalyst in a conversion reactor to form alcohols characterised in that an ether is added and reacted inside the conversion reactor.

According to a preferred embodiment, the present invention provides a process for the conversion of hydrocarbon to alcohols comprising the steps of:

1. converting a hydrocarbon feedstock into a mixture of carbon oxide(s) and hydrogen in a syngas reactor,
2. passing the mixture of carbon oxide(s) and hydrogen from the syngas reactor to a conversion reactor, and
3. reacting said mixture in said conversion reactor in the presence of a particulate modified molybdenum sulphide based catalyst and/or a modified methanol based catalyst and/or a modified Fischer-Tropsch catalyst and/or a precious metal based catalyst (e.g. rhodium) to form alcohols, characterised in that an ether(s) is added and reacted inside the conversion reactor.

For the purpose of the present invention and appending claims, "producing oxygen containing hydrocarbon compounds from a mixture of carbon oxide(s) and hydrogen (e.g. synthesis gas)", means that the oxygen containing hydrocarbons (oxygenates) represent at least 10% by weight, preferably at least 20% by weight, preferably at least 40% by weight, preferably at least 70% by weight and most preferably at least 90% by weight of the total liquid (under STP conditions) products exiting the conversion reactor.

According to a preferred embodiment of the present invention, the oxygen containing hydrocarbon compounds are alcohols and other organic oxygenates, such as ethers.

According to a further embodiment of the present invention, the alcohols comprise mainly methanol, ethanol, propanols (predominately n-propanol with low amounts of isopropanol) and butanols (predominately n-butanol and isobutanol); said methanol, ethanol, propanols and butanols preferably represent together at least 5% by weight, more preferably at least 10% by weight and most preferably at least 20% by weight of the total liquid (under STP conditions) products exiting the conversion reactor. The ethers may represent all together at least 1% by weight, more preferably at least 2% by weight of the total liquid (under STP conditions) products exiting the conversion reactor.

According to another embodiment of the present invention, water and carbon dioxide are also produced in the conversion reactor, and the said water, alcohols and ethers preferably represent together at least 50, preferably at least 80% by weight of the total liquid (under STP conditions) products exiting the conversion reactor.

According to an embodiment of the present invention, the ether(s) which are added into the conversion reactor come directly from the organic oxygenates obtained from the conversion reactor as by-products. Said ether(s) are thus preferably separated from the alcohol(s) produced in the conversion reactor and then recycled back into the said conversion reactor.

According to another preferred embodiment of the present invention, the ether which is added to the conversion reactor is a methyl, ethyl, propyl and/or butyl ether, preferably a mixture of at least two of these ethers. Preferably the ether which is added to the conversion reactor is selected from ethanol and propanol derived ether(s) such as diethyl ether, n-propyl ether, ethyl n-propyl ether, ethyl isopropyl ether, n-propyl isopropyl ether and iso-propyl ether, or even more preferably a mixture of at least two of these said ethers.

Quite surprisingly, the addition and/or recycle of even small amounts of ether to the conversion reactor have proven to be highly beneficial to the alcohol(s) selectivity, particularly the ethanol selectivity, while simultaneously increasing catalyst activity and improving operating life. The addition of larger quantities of ethers has been found to confer additional benefits of reduced water and carbon dioxide production.

Beyond these unexpected advantages, other advantages have also been found when applying the present process invention, amongst others:
  (i) less waste, less by-products and thus higher carbon efficiency.
  (ii) improved economics/efficiency, as there are fewer separations and a reduced number of storage tanks.

As indicated, the particulate catalyst used in the conversion reactor is preferably a modified molybdenum sulphide based catalyst and/or a modified methanol based catalyst and/or a modified Fischer-Tropsch catalyst and/or a precious metal based catalyst (e.g. rhodium).

Molybdenum sulphide based catalysts are preferred; these can be modified by a promoter. Promoter(s) can be added as salts during the catalyst preparation, and are preferably potassium ions (e.g. derived from a salt of potassium, such as potassium carbonate or acetate). The preferred loadings of potassium ions per molybdenum is comprised between 0.7 and 1.5, most preferably between 1.0 and 1.4.

The preferred catalyst, according to the present invention, is a molybdenum sulphide based catalysts containing cobalt, the cobalt to molybdenum molar ratio being preferably comprised between 0.5 and 3.0, more preferably between 0.5 and 1.0 and most preferably between 0.5 and 0.9.

According to another embodiment of the present invention, the ether(s) added to the conversion reactor do not come from the direct recycling of the organic oxygenate compounds produced in the said conversion reactor. Preferably, the ether(s) come from an indirect route, e.g. from the separation from the olefins obtained during a subsequent step of further chemical processing (i.e. converting the alcohols into corresponding olefins), or from a syngas to dimethyl ether process or from an etherification of methanol.

According to an embodiment of the present invention, the catalyst used in the conversion reactor can be selected to not produce any ether compound.

According to another embodiment of the present invention, the ether compound added into the conversion reactor comes from the direct recycling of the organic oxygenate compounds produced in the said conversion reactor.

According to an embodiment of the present invention, the catalyst used in the conversion reactor can be selected to produce any ether compound in addition to alcohols.

Any hydrocarbon-containing feed stream that can be converted into a feedstock comprising carbon monoxide and hydrogen, most preferably a synthesis gas (or "syngas"), is useful in the processes of the present invention. The hydrocarbon feedstock used according to the present invention is preferably a carbonaceous material, for example biomass, plastic, naphtha, refinery bottoms, smelter off gas, crude syngas (from underground coal gasification or biomass gasification), LPG, gas oil, vacuum residuals, shale oils, asphalts, various types of fuel oils, municipal waste, hydrocarbon containing process recycle streams and coal and/or natural gas; with coal and natural gas being the preferred sources and natural gas being the most preferable source.

According to a preferred embodiment of the present invention, methane is used as the hydrocarbon feedstock, to be converted into carbon oxides(s) and H2 (e.g. synthesis gas).

Processes for producing mixtures of carbon oxide(s) and hydrogen (commonly known as synthesis gas) are well known. Each method has its advantages and disadvantages and the choice of using a particular reforming process over another is governed by economic and available feed stream considerations, as well as by the desire to obtain the optimum (H2−CO2):CO+CO2) molar ratio in the resulting synthesis gas, that is suitable for further chemical processing. The synthesis gas may be prepared using any of the processes known in the art including partial oxidation of hydrocarbons, steam reforming, gas heated reforming, microchannel reforming (as described in, for example, U.S. Pat. No. 6,284,217 which is herein incorporated by reference), plasma reforming, autothermal reforming and any combination thereof.

A discussion of these synthesis gas production technologies is provided for in "Hydrocarbon Processing" V78, N.4, 87-90, 92-93 (April 1999) and/or "Petrole et Techniques", N. 415, 86-93 (July-August 1998), which are both hereby incorporated by reference.

It is also known that the synthesis gas may be obtained by catalytic partial oxidation of hydrocarbons in a microstructured reactor as exemplified in "IMRET 3: Proceedings of the Third International Conference on Microreaction Technology", Editor W Ehrfeld, Springer Verlag, 1999, pages 187-196. Alternatively, the synthesis gas may be obtained by short contact time catalytic partial oxidation of hydrocarbonaceous feedstocks as described in EP 0303438.

Preferably, the synthesis gas is obtained via a "Compact Reformer" process as described in "Hydrocarbon Engineering", 2000, 5, (5), 67-69; "Hydrocarbon Processing", 79/9, 34 (September 2000); "Today's Refinery", 15/8, 9 (August 2000); WO 99/02254; and WO 200023689.

Feedstocks comprising carbon monoxide and hydrogen, e.g., synthesis gas may undergo purification prior to being fed to any reaction zones. Synthesis gas purification may be carried out by processes known in the art. See, for example, Weissermel, K. and Arpe H.-J., Industrial Organic Chemistry, Second, Revised and Extended Edition, 1993, pp. 19-21.

The ratio of hydrogen to carbon monoxide in the reaction zone is preferably in the range of 20:1 to 0.1:1 by volume, more preferably in the range of 5:1 to 0.2:1, most preferably in the range of 1.5:1 to 0.5:1, e.g. 1:1. It has been found that the alcohol synthesis catalysts can also catalyse the water gas shift reaction. A consequence of this is that hydrogen and carbon dioxide are interconvertible with carbon monoxide and water. For high partial pressures of carbon dioxide (at or above the water gas shift equilibrium), carbon dioxide can act as a carbon monoxide source and a hydrogen sink and this can effect the apparent preferred syngas ratio Whilst the particular reaction conditions for the conversion reactor embodiments described hereinafter form preferred embodiments for the present invention, reaction conditions outside of these stated ranges are not excluded and in practice the effective reaction conditions may be any that are sufficient to produce mainly oxygen containing hydrocarbon compounds. The exact reaction conditions will be governed by the best compromise between achieving high catalyst selectivity, activity, lifetime and ease of operability, whilst maintaining: the intrinsic reactivity and the stability of the starting materials in question, as well as the desired reaction product to the reaction conditions.

In one embodiment of this invention, feedstock comprising the desired molar ratio of (H2−CO2):CO+CO2) is fed to a conversion reactor at a controlled rate and the reaction is carried out in a reaction zone under controlled conditions of temperature and pressure in the presence of a catalyst to convert the feedstock into oxygen containing hydrocarbons. The temperature in the reaction zone is selected from the range of from about 150° C. to about 400° C., preferably a temperature in the range of from about 250° C. to about 350° C. and most preferably in between 280 and 320° C.

The pressure in the conversion reaction zone may be selected from the range of from about 20 to 200 bar, preferably a pressure in the range of from about 80 to 150 bar and most preferably at between 80 and 120 bar. The hydrogen and carbon monoxide partial pressures should be sufficient to enable the production of oxygenates. The hydrogen and carbon monoxide may be fed separately to the conversion reactor or, preferably in combination, e.g. as synthesis gas.

For purposes of this invention, GHSV is gas hourly space velocity which is the rate of gas flow over the catalyst. It is determined by dividing the volume of gas (at 25° C. and 1 atmosphere) which passes over the catalyst in one hour by the volume of the catalyst.

The optimum gas hourly space velocity (GHSV) of the feedstock (liters of feedstock/hr/liter of catalyst) passing through the reaction zone can vary significantly, depending upon a variety of factors such as, for example, reaction conditions, composition of the feedstock and quantity and type of catalyst being used. The GHSV can be maintained at any rate in the range of from about 1 to about 30,000 hr−1 or more, preferably will be maintained at a rate of between about 500 and 20,000 hr−1, and most preferably will be maintained at a rate of between 1,000 and 10,000 hr−1.

The conversion to oxygen containing hydrocarbons (oxygenates) reaction can be carried out in a conversion reactor by passing the mixture of hydrogen and carbon monoxide over the conversion catalyst as a vapor phase reaction or as a liquid phase reaction, e.g. slurry reaction or trickle bed fluidized bed reactor.

The term conversion reactor as used in the present invention pertains to any appropriate reactor, e.g. a tubular reactor using a fixed bed of the catalyst. The reactants may be fed upwards or downwards to the catalyst, or a combination of both, to a fixed bed located in a tubular reactor. The reaction may be effected in a dynamic bed of the catalyst. In such a reaction, the bed of catalyst is moving such as in the case of a fluid bed of the catalyst. The conversion reactor may preferably be chosen amongst tubular, multitubular, slurry, moving bed, fluidised bed, radial bed, multibed or reactive distillation reactor. According to an embodiment of the present invention, a fixed bed reactor is used, preferably a radial bed(s) or a multitubular vapour phase reactor or a combination thereof is used. Most preferably the conversion reactor comprises a series of adiabatic fixed bed reactors operated either in a longitudinal and/or radial flow mode.

EXAMPLE 1

Catalyst Preparation

A potassium promoted cobalt molybdenum sulphide catalyst was prepared according to example "Comparison C" given in U.S. Pat. No. 4,831,060, except for the sulphidation procedure which was performed as indicated below.

Catalyst Testing:

The catalyst (14.56 g; 10 ml) was loaded into a tubular down-flow reactor (15 mm internal diameter).

Gas feeds to the reactor were set to the target composition by Mass Flow Controllers and the gases were premixed before entry to the top of the reactor. Liquids were introduced to the reactor via a HPLC pump set at the target flow rate. The gas and liquid was mixed and vaporised in the pre-heat section in the reactor. The flow rates in the reactor are given as GHSV which is defined as the volume flow of reactant gas at STP per volume of catalyst per hour.

Prior to the reaction conditions, the catalyst was subjected to the following sulphidation procedure:

1. Overnight nitrogen purge (GHSV=500 hr$^{-1}$) at 170 deg C.;

2. Feed changed to 2 mol % H2S in H2 stream and decrease in GHSV to 100 hr$^{-1}$;

3. Pressure increased to 25 barg;

4. Temperature increased to 250 deg C. at 1.0 deg C./min and held for 1 hour;

5. Temperature further increased to 320 deg C. at 1.0 deg C./min and held for 1 hour;

6. Decrease temperature to 270 deg C.;

7. Feed changed to 100% nitrogen at a GHSV of 2000 hr$^{-1}$ for purging.

After the sulphidation procedure outlined above the catalyst was brought onto stream by changing gas feed to syngas (CO:H2 ratio of 1) and a 50 ppm stream of H2S at a total GHSV of 2000 h$^{-1}$. The pressure was increased to 90 Barg and then the temperature was increased (at 1.0 deg C./min) to 310 deg C. The reaction products were analysed by an on-line Gas Chromatogram (CP9001-80-100 Mesh Carbosieve SII and 0.25 micron Innowax columns).

The reaction was allowed to run for 235 hours on stream under the above conditions. After which point a 2.5 mol % flow of methanol was fed to the reactor. At 287 hours on stream the methanol feed liquid was changed to a methanol/diethylether mixture (90:10% w/w) and the total liquid pump rate increased such that the methanol flow rate to the reactor remained constant. The additional diethylether feed introduced to the reactor was equivalent to 0.12 mol % of the total feed rate. Product rate data from each different feed period of was averaged from 20 hours after the change in feed (to allow for the feed to stabilise) to the end of each period.

The results of the experiment (summarized in Table 1) demonstrate that on addition of diethylether to the reactor feed, a clear increase in the rate of ethanol production is observed. Also, the rates of higher alcohols (i.e. propanol and butanol) were observed to significantly increase as a result of the addition of the ether. Furthermore, using the feed and product rates of diethylether, the conversion of ether was estimated to be about 60%. Within experimental error, the amount of ethanol that would be produced from the amount of converted ether corresponds to the extra amount of ethanol seen on addition of the ether.

TABLE 1

| Feed | Time Period (hours) | Average Ethanol Rate mg/hr | Average Propanol Rate mg/hr | Average Butanol Rate mg/hr | Total Alcohols $C_{2-4}$ Rate mg/hr | Average Diethylether Rate mg/hr |
|---|---|---|---|---|---|---|
| No diethylether | 255-286 | 279 | 36 | 2 | 317 | 0 |
| 0.12 mol % diethylether added | 307-333 | 365 | 56 | 4 | 425 | 32 |

The invention claimed is:

1. Process for the conversion of carbon oxide(s) and hydrogen containing feedstocks to oxygen containing hydrocarbon compounds, in the presence of a particulate catalyst comprising the step of reacting carbon oxide(s) and hydrogen in the presence of a particulate catalyst in a conversion reactor, to form products comprising oxygen containing hydrocarbon compounds; wherein one or more ether(s) selected from the group consisting of ethyl, propyl and butyl ether are added and reacted inside the conversion reactor.

2. Process according to claim 1 wherein the carbon oxide(s) and hydrogen containing feedstocks are synthesis gas or syngas, the oxygen containing hydrocarbon compounds are alcohols, the particulate catalyst is a particulate modified molybdenum sulphide based catalyst and/or a modified methanol based catalyst and/or a modified Fischer-Tropsch catalyst and/or a precious metal based catalyst.

3. Process for the conversion of hydrocarbons to alcohols comprising the steps of:
   a. converting a hydrocarbon feedstock into a mixture of carbon oxide(s) and hydrogen, in a syngas reactor,
   b. passing the mixture of carbon oxide(s) and hydrogen from the syngas reactor to a conversion reactor, and
   c. reacting said mixture in said conversion reactor in the presence of a particulate modified molybdenum sulphide based catalyst and/or a modified methanol based catalyst and/or a modified Fischer-Tropsch catalyst and/or a precious metal based catalyst to form alcohol(s), wherein one or more ether(s) selected from the group consisting of ethyl, propyl and butyl ether are added into the conversion reactor.

4. Process according to claim 1, wherein the ether which is added to the conversion reactor is a mixture of at least two of said ethers.

5. Process according to claim 1 wherein the ether is selected from ethanol and propanol derived ether(s).

6. Process according to claim 1 wherein the ether is an ethyl ether.

7. Process according to claim 1 wherein the ether is dimethyl ether.

8. Process according to claim 1, wherein the ether(s) that are added to the conversion reactor, come from the organic oxygenates obtained from the conversion reactor as direct by-products.

9. Process according to claim 8 wherein said ether is separated from the alcohols.

10. Process according to claim 1, wherein the ether compound which is added to the conversion reactor comes from an indirect route.

11. Method for increasing the ethanol and/or propanol and/or butanol selectivity of a process for the conversion of carbon oxide(s) and hydrogen containing feedstocks to oxygen containing hydrocarbon compounds in the presence of a particulate catalyst in a conversion reactor, comprising adding ethyl, propyl and/or butyl ethers to the conversion reactor to obtain said increase in selectivity.

12. Process according to claim 2 wherein the particulate catalyst is a rhodium-based catalyst.

13. Process according to claim 3 wherein the particulate catalyst is a rhodium-based catalyst.

14. Process according to claim 5 wherein the ether is selected from the group consisting of diethyl ether, n-propyl ether, ethyl n-propyl ether, ethyl isopropyl ether, n-propyl isopropyl ether, iso-propyl ether, and a mixture of at least two of these ethers.

15. Process according to claim 10, wherein the indirect route is from the separation from olefins obtained during a subsequent step of converting the alcohols into corresponding olefins.

* * * * *